United States Patent [19]
Grimm et al.

[11] 3,985,807
[45] Oct. 12, 1976

[54] ALKOXY DERIVATIVES OF HYDROXY AMINIMIDES

[75] Inventors: Robert A. Grimm, Upper Arlington; Owen Portwood, Columbus; Edward A. Sedor, Worthington; Jeannene A. Williams, Columbus, all of

[73] Assignee: Ashland Oil, Inc., Ashland, Ky.

[22] Filed: Mar. 31, 1975

[21] Appl. No.: 563,943

[52] U.S. Cl. .................. 260/561 B; 252/526; 252/529; 252/545; 252/548; 260/404.5; 260/557 B; 260/557 H; 260/558 P; 260/558 H; 260/561 H; 260/561 N; 526/212; 526/263; 526/265; 526/304

[51] Int. Cl.² .............. C07C 103/30; C07C 103/32; C07C 103/56

[58] Field of Search .......... 260/404.5, 558 R, 561 B

[56] References Cited
UNITED STATES PATENTS

| | | | |
|---|---|---|---|
| 3,485,806 | 12/1969 | Bloomquist et al. | 260/561 B |
| 3,803,220 | 4/1974 | Gasman | 260/404.5 |
| 3,832,367 | 8/1974 | Heiba et al. | 260/561 B |
| 3,839,372 | 10/1974 | Schneider | 260/561 B |
| 3,850,969 | 11/1974 | Grimm et al. | 260/404.5 |

OTHER PUBLICATIONS

McKillip, W. J. et al., "The Chemistry of Aminimides" Chem. Rev. 73(3) (1973) pp. 255–281.
"Ethylene Oxide" Tehnical Bulletin of Jefferson Chemical Co. Inc. (1956) p. 16.

*Primary Examiner*—Helen M. McCarthy

[57] ABSTRACT

Compounds having a moiety of the formula:

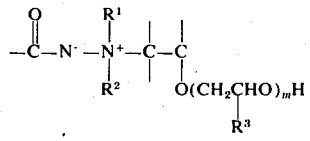

6 Claims, No Drawings

ALKOXY DERIVATIVES OF HYDROXY AMINIMIDES

BACKGROUND OF THE INVENTION

1. Field of the Invention

This invention relates to hydrolytically stable alkoxylated derivatives of 2-hydroxyalkyl substituted aminimides.

2. Description of the Prior Art

Aminimide chemistry has been extensively studied in recent years. The most comprehensive survey of this field of technology can be found in Chemical Reviews Vol. 73, p. 255 (1973).

One of the classes disclosed in the literature is the hydroxyalkylaminimides, which is distinctive in having a hydroxyalkyl group on the tertiary nitrogen. This class of compounds is depicted by Formula I.

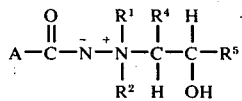

Compounds of the foregoing type are convenient starting materials for the compounds of this invention, and are most easily prepared by the method described in U.S. Pat. No. 3,485,806.

During the early investigations of aminimide technology, the aminimide corresponding to Formula I were thought to be hydrolytically stable. Those aminimides having no hydroxy group in the 2- position on the alkyl group attached to the nitrogen (Formula II, where R is alkyl) were found experimentally to be stable to base.

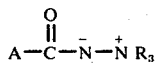

As reported in Chemical Reviews Vol. 73 p. 267 (1973), aminimides of Formula II where R is alkyl and A is phenyl were unaffected by boiling with 6 N sodium hydroxide for 24 hours.

It had been assumed that the hydroxyalkylaminimides of Formula I are equally as resistant to base hydrolysis. Thus, the literature has not pointed out any tendency of hydroxyalkylaminimides toward hydrolytic instability. This assumption was based on theory and also on preliminary performance data.

There was no theoretical basis to expect the hydroxyalkyl aminimide of Formula I to be less resistant to base attack than the trialkylaminimide of Formula II. The hydroxy group would not be expected to affect the electrophilicity of the carbonyl carbon. Nor would one expect that removal of a proton from the hydroxy group by base would cause degradation of the aminimide moiety. Further, performance data indicated that hydroxyalkyl aminimides of Formula I (A = alkyl with carbon chain of 11, 13, 15 or 17 carbon atoms, $R^1$ and $R^2$ = methyl, $R^4$ = H, $R^5$ = methyl) were useful surfactants and exhibited no apparent degradation in 23% aqueous sodium hydroxide.

Based on the accepted theoretical considerations of aminimide chemistry and in light of the published performance data, it had been assumed that the hydroxyalkylaminimides of Formula I, while having surfactant properties different from those of the trialkylaminimides of Formula II, had hydrolytic stability equal to that of the trialkylaminimides.

Contrary to the early preliminary observations, it has recently been found that the hydroxyalkylaminimides of Formula I do suffer from hydrolytic degradation with time. For example, the compound having the structure of Formula III;

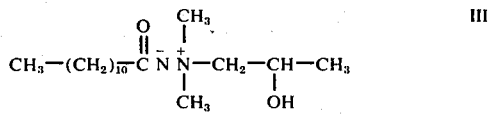

was found to be stable as a 5% aqueous solution for at least 63 days, but suffered 34% decomposition at room temperature after 230 days. Many potential applications for aminimides depend on hydrolytic stability over an extended period of time; wide commercial use of aminimides as surfactants requires a shelf life (stability) of at least 2 years. Table I shows the data for the decomposition of the compound of Formula III at reflux at a 5% concentration in IN NaOH.

Table I

| Hours at reflux | Percent decomposition |
|---|---|
| 2 | 26.3 |
| 3 | 29.0 |
| 4 | 39.5 |
| 5 | 47.4 |
| 6 | 55.3 |
| 24 | 94.7 |

Table Ia shows data for the decomposition of the compound of Formula III as a 5% dispersion in distilled water at 180° F.

Table Ia

| Hours at 180° | Percent decomposition |
|---|---|
| 10 | 14 |
| 16 | 27 |
| 24 | 47 |
| 32 | 68 |

Table II shows the decomposition of the Compound of Formula III at room temperature at a 5% concentration in NaOH.

Table II

| Days | % decomposition |
|---|---|
| 13 | 2.6 |
| 26 | 5.3 |
| 33 | 7.9 |
| 40 | 18.4 |

The mechanism of this hydrolytic degradation is unknown, and therefore the stabilization of hydroxyalkylaminimides to hydrolysis presented difficulty. Because of the resonance possibilities in aminimides, there are three possible sites for reaction when electrophillic reactants are used. These points of attack are the carbonyl oxygen in the enol form (A), the negatively charged nitrogen of the aminimide (B), and the alkoxide ion formed by reaction with base (C).

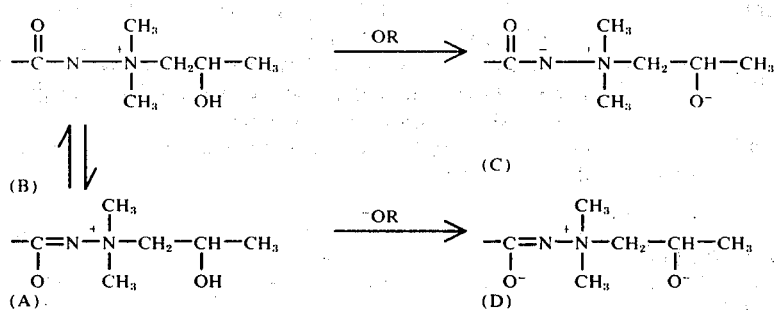

Reaction at either site (A) or (B) would destroy the basic aminimide structure and would also destroy the inner salt configuration thought to be responsible for the properties of aminimides.

SUMMARY OF THE INVENTION

In accordance with the present invention, it has been found that alkoxylation of the hydroxylkylaminimides of Formula I proceeds smoothly to yield new compounds of Formula IV, and that these alkoxylated aminimides show significantly improved hydrolytic stability. The alkoxylation proceeds according to standard alkoxylation procedures well known to the art. Any of the alkoxylating agents known to the art may be used. Lower chain length alkylene oxides are preferred in this invention, and ethylene and propylene oxides (alone, as mixtures, or added sequentially) are most preferred.

DESCRIPTION OF THE PREFERRED EMBODIMENTS

The hydroxy alkyl aminimide starting materials were prepared according to the procedures disclosed in U.S. Pat. No. 3,485,806. The following examples describe the procedure for the conversion of the hydroxyalkylaminimides of Formula I to the corresponding alkoxylated compounds of this invention. All these preparations used an autoclave equipped with a stirrer, means for heating and cooling the reactants, ports for adding or removing reactants and gases, and temperature and pressure recording devices.

EXAMPLE 1

To a two-liter autoclave was added 348g (bis-dimethyl-2-hydroxyethylamine) azelaimide, 400 g t-butyl alcohol, 0.4g sodium t-butoxide and 88g of ethylene oxide. The reactor was stirred and heated to 105° C until the pressure drop ceased. The product was stripped at 70° C to give 428g of final product as a pale yellow oil. The IR spectrum shows the characteristic aminimide absorptions at 1570 cm$^{-1}$ and thin-layer chromatography shows there are no ethylene glycols in the product.

EXAMPLE 2

To a two-liter reactor was charged dimethyl-2-hydroxypropylamine methacrylimide (119g), potassium t-butoxide (0.5g), and t-butyl alcohol (160g). The reactor was flushed with nitrogen and heated to 100° C. Ethylene oxide (132g) was then added gradually from a separate tank taking care not to exceed 50 psig. When the pressure drops, cool the reactor, neutralize with acetic acid and strip solvent to give 227g of the dimethylpoly(ethyleneoxyl) amine methacrylimide.

EXAMPLE 3

To a two-liter autoclave was charged dimethyl-2-hydroxypropylamine methacrylimide (186g), t-butyl alcohol (300g), potassium t-butoxide (1g) and propylene oxide (300g) and the mixture was blanketed with nitrogen and the contents were placed under a residual nitrogen pressure of six pounds. The contents were heated to 99° C until the pressure drop ceased. The contents were then cooled and vacuum stripped to give 347g of the product as a pale yellow oil.

EXAMPLE 4

Into a two-liter autoclave was charged dimethyl-2-hydroxypropylamine laurimide (300g) and a solution of sodium methylate in methanol (25%, 4 grams) and the unit was sealed, evacuated (27 mm) and heated to 97°C for 1 hour to remove methanol. The autoclave was then flushed with nitrogen and left with a 6 psig pressure of nitrogen. Propylene oxide (232g) was then fed into the autoclave at 97°C while keeping the pressure at 70 psig. After 24 hours the pressure was stable and the reactor contents were emptied and the golden colored product (527g, 99.4%) was collected. Hydroxyl value: Theory 105, Found 130.

EXAMPLE 5

By the procedure of Example 4, dimethyl-2-hydroxypropylamine myristimide was ethoxylated with five equivalents of ethylene oxide to give a 97% yield of golden-brown product. Thin layer chromatography showed only a trace of polyols. OH Value: Theory 102, Found 158.

EXAMPLE 6

The procedure of Example 5 was followed except that 10 equivalents (moles of ethylene oxide) was added.

EXAMPLE 7

Dimethyl-2-hydroxypropylamine laurimide (751g) and sodium methoxide (8.4g in a 25% sodium methoxide solution) were charged to an autoclave. The mixture was heated to 90° C and vacuum stripped at 20 mm pressure for 1 hour. Ethylene oxide (550g) was then added at 95° C and 60psig. The product was a cloudy liquid with a hydroxyl value of 116 (Theory for 5 mole adduct is 108).

EXAMPLE 8

The procedure of Example 7 was followed except that 10 moles of ethylene oxide was added. The product was a cloudy liquid having a hydroxyl number of 114.

EXAMPLE 9

The procedure of Example 8 was followed except that dimethyl-2-hydroxypropylamine palmitimide was used in place of the laurimide.

Table III shows the experimental data for compounds prepared according to this invention.

In order to determine the effect of alkoxylation on the hydrolytic stability of hydroxyaminimides, the product of Example 7 was compared to the starting material for Example 7 and also to the corresponding aminimide having no hydroxyalkyl group (Formula II). Storage of these compounds at 180° F for 24 hours showed no decomposition of the alkoxylated product of Example 7 or for the corresponding aminimide having no hydroxyalkyl group (Formula II). The hydroxyalkylaminimide starting material of Example 7, however, showed decomposition within 24 hours by titration and confirmed by thin layer chromatography. The percent hydrolysis was determined by precipitation of the aminimides from a solution using 50% excess standardized sodium lauryl sulfate (about 0.1 N in water). The aminimide-anion precipitate was extracted with chloroform, and the excess sodium lauryl sulfate still in solution was backtitrated with a standardized solution of a cationic (such as cetyl pyridinium bromide) using methylene blue as the end point indicator. Alkoxylation was shown to have prevented the hydrolytic decomposition of the hydroxyalkylaminide.

phosphate built systems, 0.25% surfactant based on water was used; in non-built systems the surfactant level was 0.025% based on water. Water hardness was based on parts-per-million as calcium and magnesium ion.

Although there were some slight differences found between those alkoxylated products of the invention which were prepared from recrystallized aminimide starting material and products prepared from technical grade (not recrystallized) no significant differences are found.

The product of Example 2 (dimethyl-2-hydroxyalkoxypropylamine methacrylimide) can be used as a monomer for the preparation of homopolymers or copolymers. Table V shows the reaction conditions for the copolymerization of the product of Example 2 with N-vinypyrollidone (NVP) and with 4-vinyl-pyridine (4VP).

The copolymerization may be represented as follows:

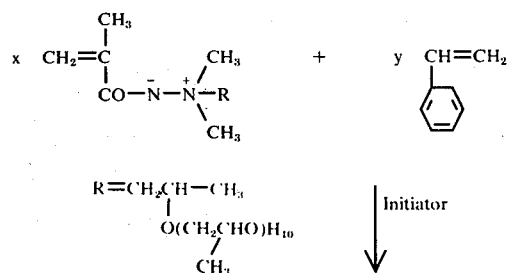

TABLE III

Alkoxylation of Aminimides

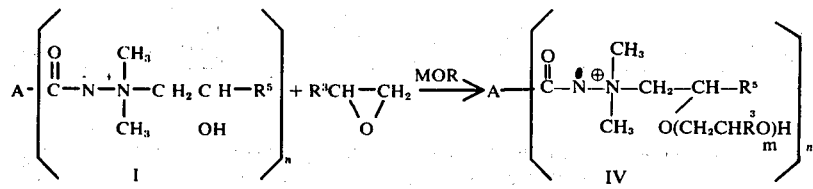

| Example | n | R⁵ | A | R³ | I gms | moles | gms | moles | MOR gms | butanol gms | Reaction temp°C | PSI |
|---|---|---|---|---|---|---|---|---|---|---|---|---|
| 1 | 2 | H | —(CH₂)₇— | H | 348 | 1 | 88 | 2 | 0.4¹ | 400 | 105 | |
| 2 | 1 | CH₃ | CH₂=CH— | H | 119 | 0.6 | 132 | 3 | 0.5¹ | 160 | 100 | 50 |
| 3 | 1 | CH₃ | CH=CH—CH₃ | CH₃ | 186 | 1 | 300 | 5 | 1.0¹ | 300 | 99 | 6 |
| 4 | 1 | CH₃ | CH₃(CH₂)₁₀ | CH₃ | 300 | 1 | 232 | 4 | 4.0² | | 97 | 70 |
| 5 | 1 | CH₃ | CH₃(CH₂)₁₂ | H | 328.5 | 1 | 220 | 5 | 4.0² | | 97 | 60 |
| 6 | 1 | CH₃ | CH₃(CH₂)₁₂ | H | 328.5 | 1 | 440 | 10 | 4.0² | | 97 | 70 |
| 7 | 1 | CH₃ | CH₃(CH₂)₁₀ | H | 751 | 2.5 | 550 | 11 | 8.4² | | 95 | 60 |
| 8 | 1 | CH₃ | CH₃ (CH₂)₁₀ | H | 751 | 2.5 | 440 | 10 | 8.4 | | 95 | 60 |
| 9 | 1 | CH₃ | CH₃—(CH₂)₁₄ | H | 891 | 2.5 | 440 | 10 | | | | |

¹MOR = potassium butoxide
²MOR = sodium methoxide

Evaluation of the alkoxylated aminimides of this invention for surface activity generated the data shown in Table IV. The surface and interfacial tensions (ASTMD-1331-56), the Ross-Miles Pour Foam heights (ASTMD-1173-53), the detergency data (ASTMD3050-72T) and the Canvas Disk wetting data were determined by methods described in *Detergency Evaluation and Testing*, J. C. Harris; Interscience, New York 1954. The Terg-O-Tometer used for the detergency evaluation was run at 125 cycles/minutes. Standard U.S. Testing soiled cotton fabric was used. In

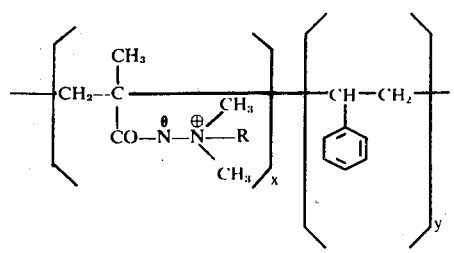

TABLE IV

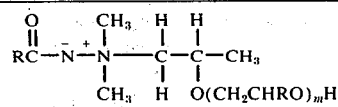

|  | $CH_3(CH_2)_{10}-$ M=O | | $CH_3-(CH_2)_{12}-$ M=O | | $CH_3(CH_2)_{14}-$ M=O | | Product of Example 7 | |
|---|---|---|---|---|---|---|---|---|
| Concentration (% by wt) | 0.1 | 0.025 | 0.1 | 0.025 | 0.1 | 0.025 | 0.1 | 0.025 |
| Surface Tension Dynes/cm | 33.3 | 32.7 | 3.0 | 3.3 | 36.2 | 36.9 | 40.9 | 41.2 |
| Interfacial Tension Dynes/cm | 4.2 | 4.2 | 3.0 | 3.3 | 3.3 | 4.1 | 10.3 | 13.8 |
| Canvas Disc Wetting Seconds | 6.0 | 106 | 12.0 | >180 | 105 | >180 | 73 | >180 |
| Aqueous pH 25° C | 7.5 | | 8.0 | | 7.0 | | 7.5 | |
| Ross-Miles Foam Test* 25° C | 160 | 105 | 75 | 75 | 15 | 20 | 110 | 85 |
| (millimeters) Initial 5 Min. | 145 | 100 | 70 | 70 | 10 | 19 | 75 | 50 |
| Ross-Miles Foam Test 50° C | 165 | 95 | 25 | 37 | 20 | 15 | 65 | 15 |
| (millimeters) Initial 5 Min. | 20 | 25 | 20 | 32 | 15 | 12 | Tr | Tr |
| Detergency | DW | 100PPM | DW | 100PM | DW | 100PPM | DW | 100PPM |
| % Soil Removal | | | | | | | | |
| Built System | 24.8% | 21.3% | 19.4% | 14.7% | 20.6% | 19.6% | 18.4% | 16.8% |
| Non-Built System | 3.9% | — | 8.5% | — | 11.2% | — | 6.1% | 8.2% |
| Cloud Points-High | 50° C | | 43° C | | 26° C | | >85° C | |
| 1% Solutions - Low | <0° C | | <0° C | | 19° C | | <6° C | |

|  | Product of Example 4 | | Product of Example 8 | | Product of Example 5 | | Product of Example 6 | | Product of Example 9 | |
|---|---|---|---|---|---|---|---|---|---|---|
| Concentration *% by wt) | 0.1 | 0.025 | 0.1 | 0.025 | 0.1 | 0.025 | 0.1 | 0.025 | 0.1 | 0.025 |
| Surface Tension Dynes/cm | 33.5 | 32.7 | 37.3 | 40.3 | 41.5 | 42.0 | 42.5 | 42.6 | 34.6 | 34.2 |
| Interfacial Tension Dynes/cm | 6.0 | 7.0 | 6.4 | 10.5 | 10.0 | 11.5 | 8.9 | 9.2 | 7.0 | 10.7 |
| Canvas Disc Wetting Seconds | 7.2 | 110 | >180 | 180 | 6.0 | >180 | >180 | >180 | 16.2 | 112.7 |
| Aqueous pH 25° C | 8.2 | | 7.7 | | 8.6 | | 8.1 | | 7.9 | |
| Ross-Miles Foam Test* 25° C | 70 | 23 | 70 | 20 | 110 | 70 | 95 | 65 | 77 | 40 |
| (millimeters) Initial 5 min. | Tr | Tr | 5 | N | 20 | 25 | 10 | 13 | 35 | 27 |
| Ross-Miles Foam Test 50° C | Tr | Tr | 25 | 5 | 130 | 75 | 90 | 60 | Tr | Tr |
| (millimeters) Initial 5 min. | N | N | N | N | 5 | Tr | Tr | Tr | N | N |
| Detergency | DW | 100PPM | DW | 100PPM | DW | 100PPM | DW | 100PPM | DW | 100PPM |
| % Soil Removal | | | | | | | | | | |
| Built System | 19.0% | 12.3% | 17.3% | 16.0% | 22.0% | 21.3% | 20.2% | 18.8% | 16.6% | 15.8% |
| Non-Built System | 7.9% | 5.7% | 8.0% | 7.4% | 11.8% | 8.5% | 12.0% | 9.2% | 6.5% | 4.9% |
| Cloud Points-High | 35–37° C | | >85° C | | >90° C | | >90° C | | 32–35° C | |
| 1% Solutions-Low | <1° C | | <6° C | | <9° C | | <10° C | | <1° C | |

*Foam Heights: Tr=Trace, N=None

These new copolymers are useful in adhesive applications and coatings.

The following example illustrates the synthesis and utility of a copolymer.

EXAMPLE 10

Under a nitrogen atmosphere, 22.4 parts of 1,1-dimethyl-1-(2-hydroxalkoxypropyl) amine methacrylimide (Example 2), 8.4 parts 4-vinylpyridine, 31 parts 2-propanol and azoisobutyronitrile (AIBN) were sealed in a 200 ml Wheaton-bottle. After stirring magnetically for 4 hours in a thermostatic bath at 70°C, the polymerization solution was yellow and very viscous. The crude polymer was purified by dissolving with methanol and reprecipitating with acetone. The infrared absorption spectrum of the copolymer had absorption bands indicative of aminimide and 4-vinylpryidine residues. A methanol (85 parts) solution of the polymer (15 parts) was used to coat single strand brass-plated wire which had been cleaned with perchloroethylene. The coated wire cord was baked at 230° C for 80 seconds. The coated cord was next treated with a second dip consisting of an aqueous medium containing a resorcinol/formaldehyde resin/rubber latex composition; the rubber latex composition comprising a butadiene/styrene vinylpyridine terpolymer. The coated wire cord was again heat treated for 80 seconds at 230° C. The treated wire cord was next embedded in a rubber stock mixture (cold skim stock containing resorcinol formaldehyde resin) and vulcanized. The strength of adhesion of the vulcanized rubber to the wire cord was determined according to ASTM Designation D2229 –63T. The maximum force required to separate the wire from the rubber at room temperature was 32.6 + 3.5 for the polymer of Example 12 and 29.7 + 2.4 for Example 13.

Table V shows data for representative copolymerizations of alkoxylated aminimide.

The capping technique disclosed in U.S. 3,485,806 Column 8 Line 72 was pointed, in that disclosure, toward preventing the reaction of the hydroxyamine byproduct with the isocyanate produced by thermolysis:

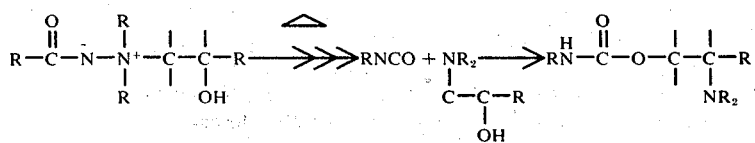

TABLE V
CO-POLYMERIZATION OF DIMETHYL-2-HYDROXYALKOXYPROPYLAMINE METHACRYLIMIDE

| Example | CoMonomer | Feed Mole % | Solvent % N.V. | Temp. °C | Time min. | Conv. % | Compos Mole % | Viscosity inh[a] |
|---------|-----------|-------------|----------------|----------|-----------|---------|---------------|------------------|
| 10 | NVP | 38–62 | 2PrOH 60% | 70 | 5 | 69 | 41–59 | 0.18 |
| 11 | 4VP | 38–62 | 2PrOH 70% | 70 | 5 | 34 | 15–85[b] | 0.12 |
| 12 | NVP | 42–58 | 2PrOH 60% | 75 | 5 | 85 | 35–65 | 0.16 |
| 13 | NVP | 61–39 | 2PrOH 60% | 75 | 7 | 67 | 48–52 | 0.09 |

[a]Inherent Viscosity - 5 g. diluted in McOH.
[b]Estimated
[c]Initiator AIBN1%

This reaction obviously interferes with the desired reaction of the isocyanate with other disfunctional monomers, preventing the formation of desired polymers. As disclosed in 3,485,806, capping with a monobasic acid anhydride would lead to an ester.

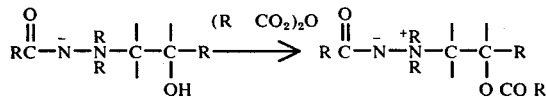

To determine whether this type of capping would also improve hydrolytic stability in addition to the disclosed benefit of preventing the undesired side reaction, esterification of a hydroxyaminimide was carried out as shown in Examples 14 and 15.

EXAMPLE 14

Dimethyl-2-hydroxypropylamine palmitimide (142.8 g; 0.4 mole) in methyl ethyl ketone was heated in a 1 liter flask until dissolved, and acetic anhydride (42 g; 0.4 mole) was added over a five minute period. The mixture was heated over steam for 15 minutes, allowed to cool, and stripped to high vacumn. The product was tested for hydrolytic stability.

This ester at 180° F for 144 hours, had suffered 40% decomposition.

EXAMPLE 15

Succinic anhydride (50g) and acetonitrile (250ml) were charged to a reaction flask. A solution of dimethylhydroxypropyl lauryoyl aminimide (starting material for Example 7) (150g) in acetonitrile (250 ml) was added, and the solution was held at 50°C for 4 hours. The acid/ester product crystallized out. Calculated for $C_{21}H_{40}N_2O_5$; C 62.97; H 10.07; N 6.99; Found C 64.13; H 9.90; N 7.17. This compound was neutralized with NaOH and was found to be unstable at a 5% concentration in water; after 19 hours at 120°F there was 18% decomposition. After 48 days at room temperature there was 18% decomposition.

Thus the esterification procedure suggested in U.S. Pat. No. 3,485,806 as a means of tying up the free hydroxyls to prevent the reaction with isocyanate is not applicable to the stabilization of the hydroxyalkyl aminimides to hydrolytic degradation.

What is claimed is:
1. A compound having the formula:

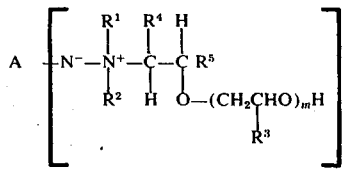

wherein:
$R^1$ and $R^2$ represent the same or different alkyl, cycloalkyl or aralkyl radicals or together represent the single divalent organic radical; $R^4$ and $R^5$ are independently selected from the group consisting of hydrogen, alkyl, cyloalkyl, aryl, aralkyl, alkaryl, and alkoxyalkyl;
A is a carboxylic acid residue attached to the indicated nitrogen atom by the carbonyl group of the acid;
$R^3$ = alkyl, alkoxyalkyl or hydrogen;
n is an integer of from 1 to 5; and
m = 1 - 15
2. The compound of claim 1 wherein n is 2; A is a di-carboxylic acid residue having 2 to 36 carbon atoms; $R^1$ and $R^2$ are methyl; $R^4$ is hydrogen and $R^5$ is methyl or hydrogen.
3. The compound of claim 1 wherein n is 1; A is a carboxylic acid residue having 2-22 carbon atoms; $R^1$ and $R^2$ are methyl; $R^4$ is hydrogen; and $R^5$ is an alkyl group having 1 to 10 carbon atoms or hydrogen, and $R^3$ is methyl or hydrogen.
4. The compound of claim 3 wherein $R^5$ is methyl or hydrogen.
5. The compound of claim 4 wherein A is methacroyl.
6. The compound of claim 3 wherein A is a fatty acid residue.

* * * * *